(12) United States Patent
Qin et al.

(10) Patent No.: US 11,739,494 B2
(45) Date of Patent: Aug. 29, 2023

(54) DEVICE FOR CENTRIFUGE TESTING OF DRIVEN PILE IN DIFFERENT INSTALLATION AND PULL-OUT MODES AND OPERATION METHOD THEREFOR

(71) Applicant: Wenzhou University, Wenzhou (CN)

(72) Inventors: Wei Qin, Wenzhou (CN); Jun Wang, Wenzhou (CN); Junfeng Ni, Wenzhou (CN); Ziyang Gao, Wenzhou (CN); Ning Fan, Wenzhou (CN)

(73) Assignee: Wenzhou University

( * ) Notice: Subject to any disclaimer, the term of this patent is extended or adjusted under 35 U.S.C. 154(b) by 24 days.

(21) Appl. No.: 17/411,129

(22) Filed: Aug. 25, 2021

(65) Prior Publication Data

US 2022/0064896 A1 Mar. 3, 2022

(30) Foreign Application Priority Data

Sep. 1, 2020 (CN) .......................... 202010902486.3

(51) Int. Cl.
*E02D 33/00* (2006.01)
*E02D 11/00* (2006.01)
*G01N 33/24* (2006.01)

(52) U.S. Cl.
CPC .............. *E02D 33/00* (2013.01); *E02D 11/00* (2013.01); *G01N 33/24* (2013.01)

(58) Field of Classification Search
CPC .......... E02D 33/00; E02D 11/00; G01N 33/24
See application file for complete search history.

(56) References Cited

FOREIGN PATENT DOCUMENTS

| CN | 106759540 | A | * | 5/2017 | | |
|----|-----------|---|---|--------|---|---|
| CN | 107100210 | A | * | 8/2017 | ............. | E02D 33/00 |
| CN | 107179396 | A | * | 9/2017 | ............. | G01N 33/24 |
| CN | 111610113 | A | * | 9/2020 | ............. | E02D 33/00 |
| CN | 112160349 | A | * | 1/2021 | ............. | E02D 33/00 |
| CN | 112160351 | A | * | 1/2021 | ............. | E02D 33/00 |
| CN | 214614219 | U | * | 11/2021 | ............. | E02D 33/00 |

\* cited by examiner

*Primary Examiner* — Ryan D Walsh
(74) *Attorney, Agent, or Firm* — Jason C. Cameron

(57) ABSTRACT

The present disclosure discloses a device for centrifuge testing of a driven pile in different installation and pull-out modes, including a supporting system, a pile driving system, a pile-soil system and a measurement and acquisition system. The present disclosure further provides a method for operating the device for centrifuge testing of a driven pile in different installation and pull-out modes. The present disclosure can perform geotechnical centrifuge testing of a driven pile through penetration in different installation modes and pull-out in different pull-out modes, and provide the effective test device and method for study of a pile-soil mutual dynamic response during a whole process of penetration and a process of pull-out of the driven pile. Moreover, pile-soil deformation characteristics and the like during the processes of penetration and pull-out can be visually observed through a high-speed camera or a digital camera, and the pull-out and penetration can be tested separately.

8 Claims, 9 Drawing Sheets

DEVICE FOR CENTRIFUGE TESTING OF DRIVEN PILE IN DIFFERENT INSTALLATION AND PULL-OUT MODES AND OPERATION METHOD THEREFOR

CROSS REFERENCE TO RELATED APPLICATION(S)

This patent application claims the benefit and priority of Chinese Patent Application No. 202010902486.3, filed on Sep. 1, 2020, the disclosure of which is incorporated by reference herein in its entirety as part of the present application.

TECHNICAL FIELD

The present disclosure relates to a device for centrifuge testing of a driven pile in different installation and pull-out modes, and further relates to a method for operating the device for centrifuge testing of a driven pile in different installation and pull-out modes.

BACKGROUND ART

Conventional methods for installing a driven pile usually include hammering penetration, vibration penetration and static pressure penetration. At present, research on a process of penetration and installation of a driven pile is performed mainly through a wave equation-based pile driving analysis software and field test data acquisition and analysis. However, the wave equation-based pile driving analysis software has limitations because of the problems such as the failure to analyze fluid-solid coupling during the penetration process of the pile, and the field test is restricted by factors such as an acquisition device and high economic costs. Therefore, in the process of related research, numerical analysis and laboratory tests are usually used for fine research and comparison, so as to obtain a relationship between the bearing capacity of driven piles and sizes of piles, properties of soil, etc. However, due to the limitation of the development of a numerical technology, the pile driving numerical analysis of developed at present has not been commercialized and industrialized; due to the influence of the size effect, test results of 1 g gravity laboratory tests are unreasonable to some extent. Despite of these, a geotechnical centrifuge can overcome the influence of the size effect and greatly reduce the cost of field test. Because of the high controllability of the test environment, relevant tests can be performed for many times, so that effective comparative data can be obtained, which provides a basis for more detailed and in-depth research. At present, there is a lack of a device and method for experimental research on a pile-soil dynamic response in a process of penetration of a driven pile by a relevant geotechnical centrifuge test instrument in different installation modes.

Moreover, pile hammers and model piles of conventional research devices do not have very precise and stable guidance, and the pile hammers often require a very large volume to maintain strength, so the accuracy is not enough, and the direction of force applied is often deviated.

SUMMARY

The present disclosure provides a device for centrifuge testing of a driven pile in different installation and pull-out modes. The device provides a more visual laboratory test and research means for pile-soil interaction and a dynamic response of the soil and the like in a penetration process of a driven pile, enables a relevant law response of the penetration process close to the site through a geotechnical centrifuge, and effectively guides movement of a pile hammer and a pile body through structure settings, so that the process precision of pile driving is higher, so as to acquire accurate test data. The present disclosure further provides a method for operating the device for centrifuge testing of a driven pile in different installation and pull-out modes.

For this, the device for centrifuge testing of a driven pile in different installation and pull-out modes provided in the present disclosure includes a supporting system, a pile driving system, a pile-soil system and a measurement and acquisition system.

The supporting system includes a vertical supporting system and a pile driving frame supporting system; the vertical supporting system includes a threaded rigid column, a vertical outer support frame, a vertical inner support frame and a bottom rigid plate; the vertical supporting system is configured to support an entire test model and connected to a corresponding device of the centrifuge, and at the same time provides a supporting platform for a pile driving frame in the model; the vertical outer support frame is movably connected to the threaded rigid column, and is controlled to lift by a vertical support lifting motor; the pile driving frame supporting system is configured to support the pile driving frame and includes an upper pile driving frame outer support, an upper pile driving frame inner support, a lower pile driving frame inner support, a lower pile driving frame outer support, an upper pile driving frame back support and a lower pile driving frame back support, and the pile driving frame supporting system ensures that the pile driving frame is kept stable in a pile driving process and a geotechnical centrifuge test process.

The pile-soil system includes a model pile and a model box, a pile cap is fixed at the top of the model pile and protects a pile head of the model pile in a penetration process, an element for monitoring physical and mechanical variables is attached to a pile body, the model box is a semi-cylindrical box body with a closed lower portion and an open upper portion, a semicircular portion is composed of high-strength and high-rigidity steel plates, drain holes are distributed in the box body, a semicircular section of the model box is composed of transparent plates made of a high-strength resin, soil is arranged in the model box, and a lifting motor is arranged below a fixing support and sleeves the threaded rigid column; and the lifting motor drives a nut to rotate to lift on the threaded rigid column, so as to control a height of the fixing support.

A centrifuge system includes a centrifuge, the supporting system, a full-life loading system of a driven pile and the pile-soil system are fixedly installed in a test cabin of the centrifuge, supergravity is applied to the test model through movement of the centrifuge, and a time of fluid-solid coupling is shortened in a supergravity environment to speed up a change process.

A measurement system includes a soil monitoring system 17 and a pile body monitoring system, the soil monitoring system includes a soil monitoring element, the pile body monitoring system includes a pile body monitoring element, the soil monitoring element tests an initial stress-strain of a soil sample, a pore pressure state and corresponding physical and mechanical parameters during pile driving and after installation, and the pile body monitoring element is capable of acquiring physical and mechanical parameters such as pile body deformation stress.

The pile driving system includes a pile driving frame, a pile driving device and a penetration and pull-out power device; the pile driving frame is connected to the vertical supporting system through the pile driving frame supporting system, and the pile driving device includes a pile hammer guide rail, a guide rail for a driven pile and a penetration and pull-out power device; the penetration and pull-out power device 11 is provided with a power system and a pile hammer, and a pile hammer pad is installed on a lower portion of the pile hammer; a pull-out mode is vibration pull-out or static load pull-out, a lower end of a pull-out device is provided with a hammer pad, the hammer pad conducts electricity to generate electromagnetic attraction, and a magnetic force of the hammer pad is controlled by changing a current; the pile cap is made of a magnetically attractable material, the hammer pad is magnetically attracted to the pile cap after being energized, and the pile cap, the hammer pad and the model pile are fixed to be a whole in the pull-out process.

Preferably, the pile hammer guide rail includes vertical holes for maintenance at four sides, the pile hammer is placed in the vertical hole, a center of the pile hammer guide rail is provided with the guide rail for a driven pile, two sides of the guide rail for a driven pile are connected to an inner side wall of the pile hammer guide rail through vertical rib plates, an upper side and a lower side of the guide rail for a driven pile are provided with side openings, a cross section of the pile hammer is I-shaped, the pile hammer has a downward hammering end, a section of the hammering end matches the guide rail for a driven pile, the hammering end is placed in the guide rail for a driven pile, an upper narrow part and a lower narrow part of the pile hammer are positioned at the side openings, and an upper wide part and a lower wide part of the pile hammer are attached to an inner wall of the pile hammer guide rail.

A method for operating the device for centrifuge testing of a driven pile in different installation and pull-out modes provided in the present disclosure includes the following steps:

step 1: determining a size and layout of each system of a test device, and performing test analysis of processes of penetration and pull-out of a large-diameter open pile foundation in in-situ saturated clay, where a geotechnical centrifuge is 150 kg, a pile has a diameter of 8 m, a length of 80 m and a wall thickness of 9 cm in in-situ size, the saturated clay is marine saturated clay, and a fluid therein is seawater; a model pile has a diameter of 5.34 cm, a length of 53.34 cm and a wall thickness of 0.6 mm in size, grating fiber points are evenly and symmetrically arranged on a pile body, there are 10 grating fiber points on each side, 3 columns of grating fiber miniature earth pressure cells and 3 columns of osmometers are symmetrically arranged in soil, the two kinds of test elements are arranged at intervals, there are a total of 12 columns of test elements, there are 8 elements in a height direction in each column, a model box has a diameter of 1.5 m and a height of 1.0 m in size, 10 drain holes are evenly formed in a height direction of the model box, 10 drain holes are evenly formed in a diameter direction at 4 the bottom, 15 columns of drain holes are formed in an arc direction, pile driving frames each have a length of 1.2 m and a width of 0.25 m, pile hammer guide rails and guide rails for a driven pile are evenly and symmetrically distributed on the pile driving frames, and the pile driving frames are symmetrically fixed in a vertical supporting system in a length direction;

step 2: installing a supporting system, a pile-soil system, a measurement system and a centrifuge system;

step 3: installing a pile driving system, where the model pile penetrates into the soil through hammering and is pulled out through static pressure, and a corresponding pile hammer and pull-out device are selected and servo-controlled;

step 4: performing a hammering penetration test, acquiring monitored data through a wireless acquisition system, recording a hammering penetration process through a high-definition high-speed computer, and controlling the hammering penetration of the pile hammer through wireless servo control; and step 5: after the penetration is completed, performing a long-term load-bearing performance test, and enabling a pile hammer device to be held tightly with the a pile head through servo control; after a duration which is required by the test and in which data is always acquired, converting the servo control to a pull-out mode, performing a pull-out test, acquiring relevant data through a wireless acquisition system, and recording the pull-out process with a high-speed camera.

Preferably, when hammer penetration is used, a pile pad needs to be laid for the model pile; when static pressure and vibration penetration are used, the pile pad is not required; and when vibration penetration is used, a pile cap and a pile hammer of the model pile need to be fixed.

Preferably, the vertical supporting system and a pile driving frame supporting system are made of 8 #B-12 #B high-strength I-beams anchored by rivets, and the pile driving frame supporting system and the pile driving frame are also anchored by rivets.

The technical effects of the present disclosure are as follows:

(1) The present disclosure can perform geotechnical centrifuge testing of a driven pile through penetration in different installation modes and pull-out in different pull-out modes, and provide the effective test device and method for study of a pile-soil mutual dynamic response during a whole process of penetration and a process of pull-out of the driven pile.

(2) Pile-soil deformation characteristics and the like during the processes of penetration and pull-out can be visually observed through a high-speed camera or a digital camera, and the pull-out and penetration can be tested separately.

(3) The device provides a more visual laboratory test and research means for pile-soil interaction and a dynamic response of the soil and the like in a penetration process of a driven pile, and enables a relevant law response of the penetration process close to the site through a geotechnical centrifuge.

(4) The device effectively guides movement of a pile hammer and a pile body through structure settings, so that the process precision of pile driving is higher, so as to acquire accurate test data.

DETAILED DESCRIPTION

Figure 1:
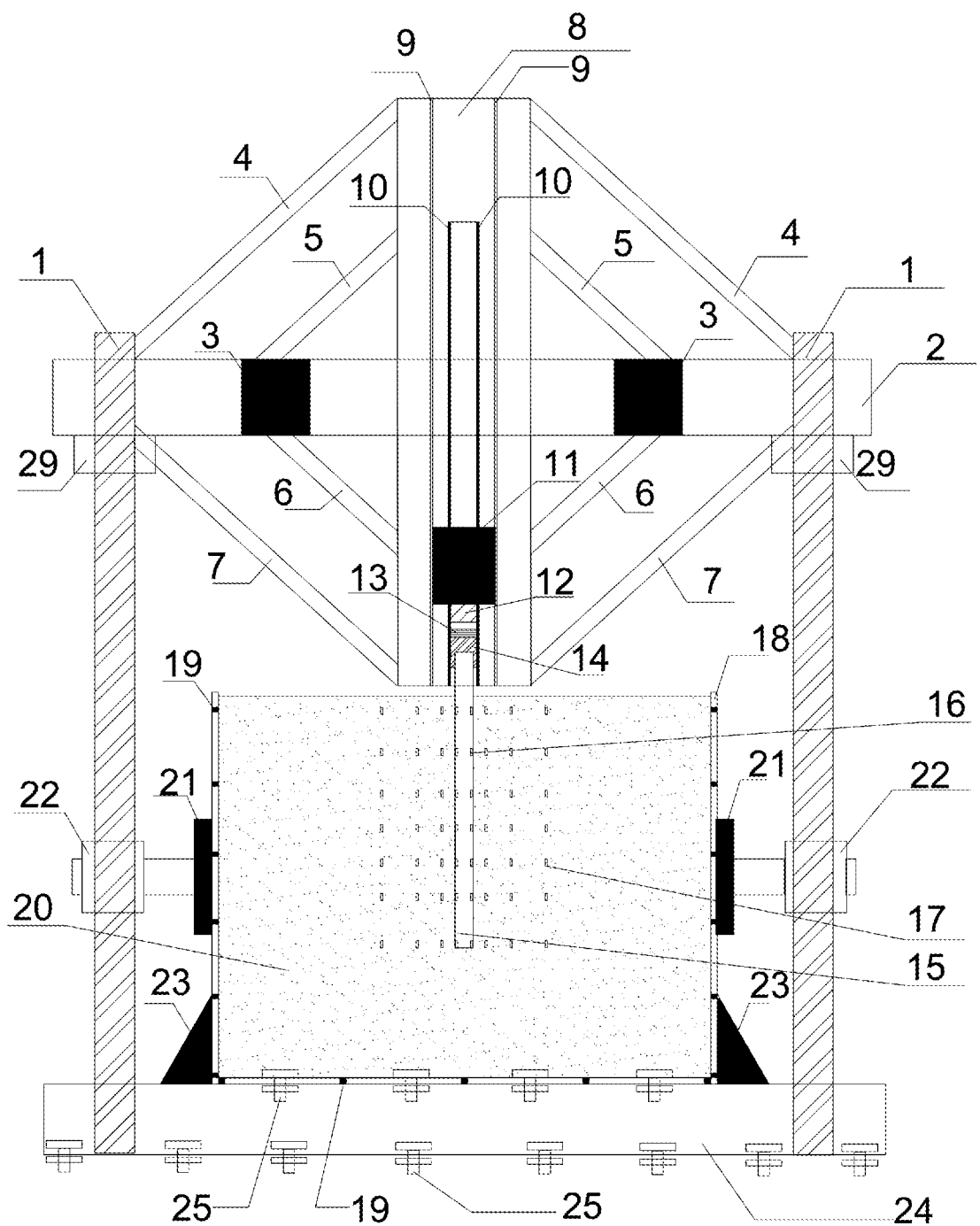
FIG. 1 is a schematic structural sectional view of a device for centrifuge testing of a driven pile in different installation and pull-out modes provided in the present disclosure.

The present disclosure will be further described in detail below with reference to accompanying drawings and embodiments. The same parts are denoted by the same reference numerals of accompanying drawings. It should be noted that the words "front", "rear", "left", "right", "upper" and "lower" used in the following description refer to the directions in the accompanying drawings, and the words "bottom surface", "top surface", "inner" and "outer" separately refer to a direction toward or away from a geometric center of a particular component.

Figure 2:
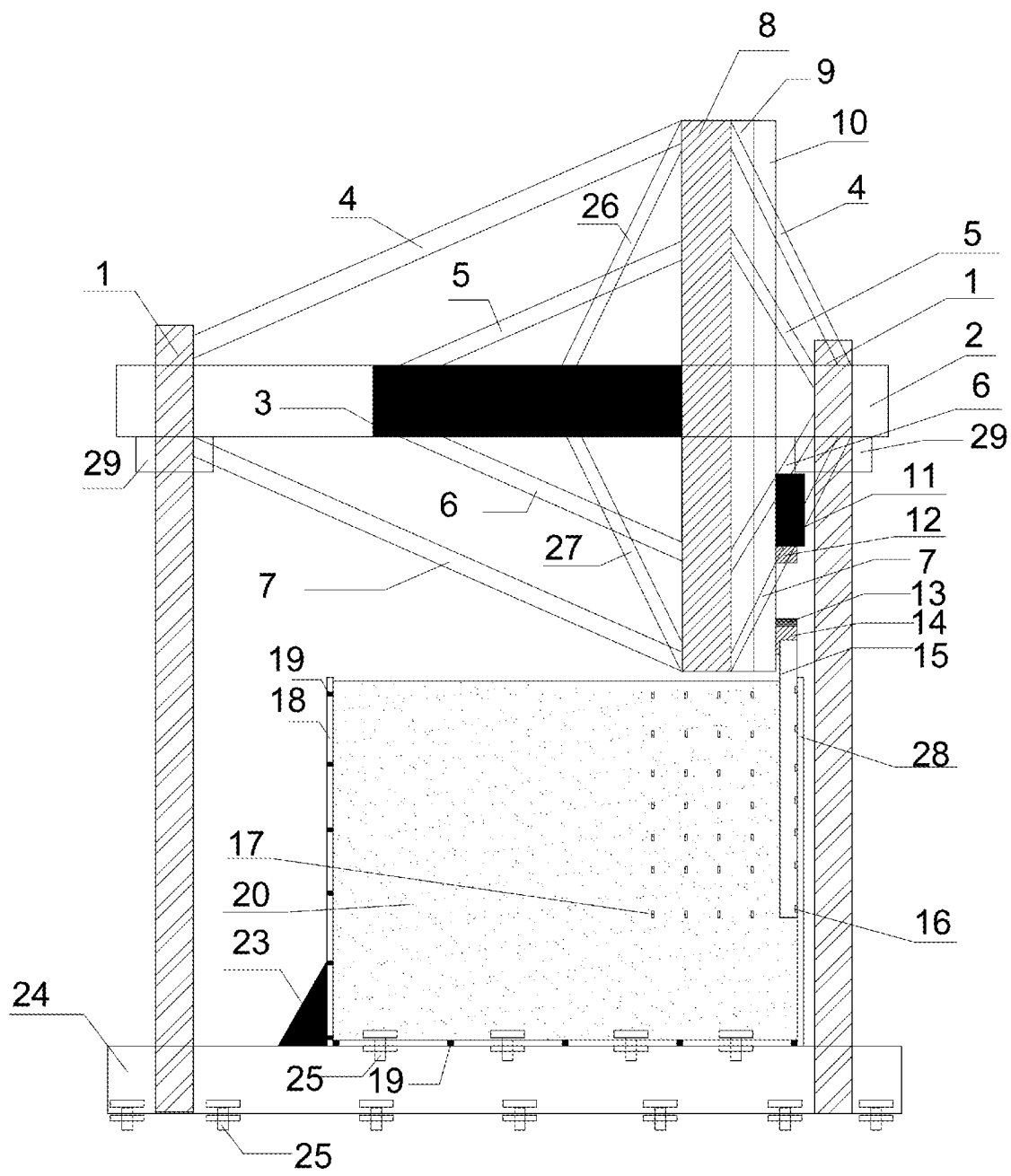
FIG. 2 is a side view of FIG. 1.
Figure 3:
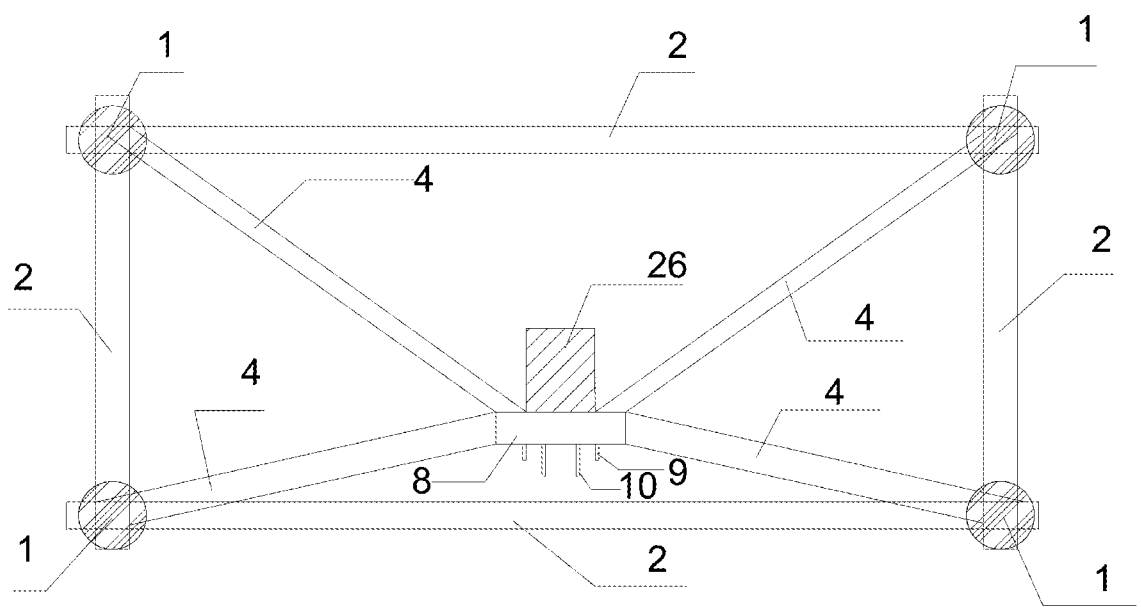
FIG. 3 is a top view of a vertical supporting system according to the present disclosure.
Figure 4:
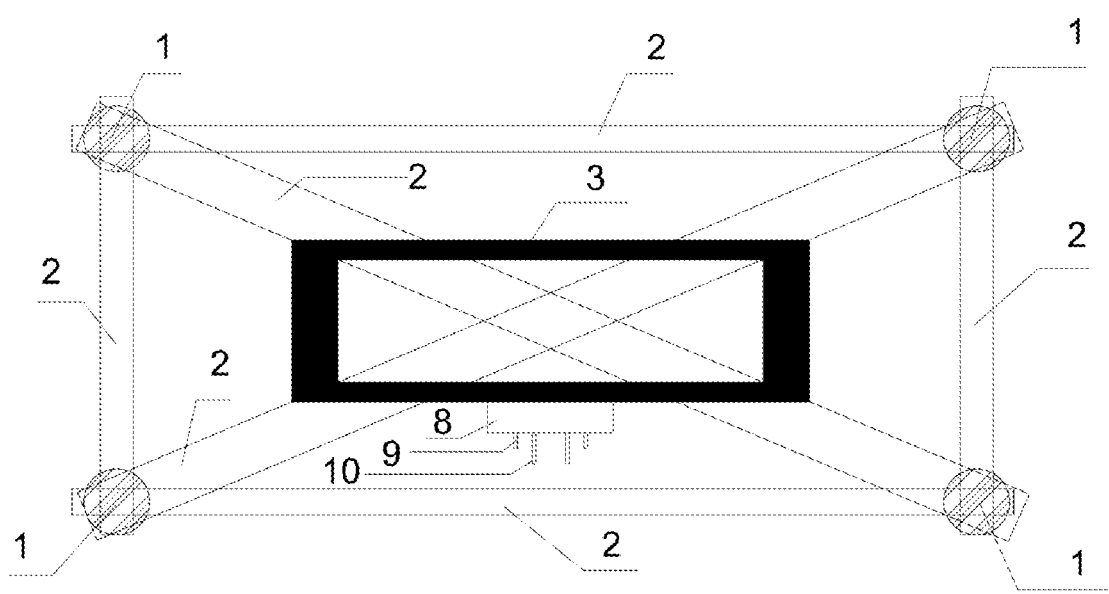
FIG. 4 is a top view of a pile driving frame supporting system according to the present disclosure.

Referring to FIG. 1 to FIG. 4, the device for centrifuge testing of a driven pile in different installation and pull-out modes provided in the present disclosure includes a supporting system, a pile driving system, a pile-soil system and a measurement and acquisition system.

The supporting system includes a vertical supporting system and a pile driving frame supporting system; the vertical supporting system includes a threaded rigid column 1, a vertical outer support frame 2, a vertical inner support frame 3 and a bottom rigid plate 24; the vertical supporting system is configured to support an entire test model and connected to a corresponding device of the centrifuge, and at the same time provides a supporting platform for a pile driving frame in the model; the vertical outer support frame 2 is movably connected to the threaded rigid column 1, and is controlled to lift by a vertical support lifting motor 29; the pile driving frame supporting system is configured to support the pile driving frame and includes an upper pile driving frame outer support 4, an upper pile driving frame inner support 5, a lower pile driving frame inner support 6, a lower pile driving frame outer support 7, an upper pile driving frame back support 26 and a lower pile driving frame back support 27, and the pile driving frame supporting system ensures that the pile driving frame is kept stable in a pile driving process and a geotechnical centrifuge test process.

The pile-soil system includes a model pile 15 and a model box 18, a pile cap 14 is fixed at the top of the model pile 15 and protects a pile head of the model pile in a penetration process, elements for monitoring physical and mechanical variables (pile body stress-strain, etc., such as a pile body monitoring element 16 and a grating fiber monitoring element) are attached to a pile body, the model box 18 is a semi-cylindrical box body with a closed lower portion and an open upper portion, a semicircular portion is composed of high-strength and high-rigidity steel plates, drain holes 19 are distributed in the box body, a semicircular section of the model box 18 is composed of transparent plates 28 made of a high-strength resin, soil 20 is arranged in the model box 18, and a lifting motor 22 is arranged below a fixing support 21 and sleeves the threaded rigid column 1; and the lifting motor 22 drives a nut to rotate to lift on the threaded rigid column 1, so as to control a height of the fixing support 21.

A centrifuge system includes a centrifuge, the supporting system, a full-life loading system of a driven pile and the pile-soil system are fixedly installed in a test cabin of the centrifuge, supergravity is applied to the test model through movement of the centrifuge, and a time of fluid-solid coupling is shortened in a supergravity environment to speed up a change process.

A measurement system includes a soil monitoring system and a pile body monitoring system, the soil monitoring system includes a soil monitoring element 17, the pile body monitoring system includes the pile body monitoring element 16, the soil monitoring element 17 tests an initial stress-strain of a soil sample, a pore pressure state and corresponding physical and mechanical parameters during pile driving and after installation, and the pile body monitoring element 16 is capable of acquiring physical and mechanical parameters such as pile body deformation stress.

The pile driving system includes a pile driving frame 8, a pile driving device and a penetration and pull-out power device 11. The pile driving device is a mechanism that applies force to a pile and includes a pile hammer, a vibration hammer, a static pressure device, and the like. The pile driving frame 8 is made of special rigid steel plates. The pile driving frame 8 is connected to the vertical supporting system through the pile driving frame supporting system and marked with a ruler. The ruler on the pile driving frame 8 enables a tester to effectively grasp the data on entry of the pile body in a test process so as to combine with other data to form a data model. The pile driving device includes a pile hammer guide rail 9, a guide rail 10 for a driven pile and a penetration and pull-out power device 11. The penetration and pull-out power device 11 is provided with a power system and a pile hammer, and according to difference in penetration modes and pull-out modes, a hammering hammer, a vibration hammer or a static pressure hammer may be selected as the penetration and pull-out power device 11. The hammering hammer may be a hydraulic hammer, taking diesel hydraulic pressure or electromagnetic shock as power. A pile hammer pad 12 is installed on a lower portion of the pile hammer. A pull-out mode is vibration pull-out or static load pull-out, a lower end of a pull-out device is provided with a hammer pad, the hammer pad conducts electricity to generate electromagnetic attraction, and a magnetic force of the hammer 7 pad is controlled by changing a current; the pile cap is made of a magnetically attractable material, the hammer pad is magnetically attracted to the pile cap after being energized, and the pile cap, the hammer pad and the model pile are fixed to be a whole in the pull-out process. The fixing method is implemented by an automatic clamping device to ensure the stability of the pile driving process, and this fixing method pertains to the prior art.

Figure 5:
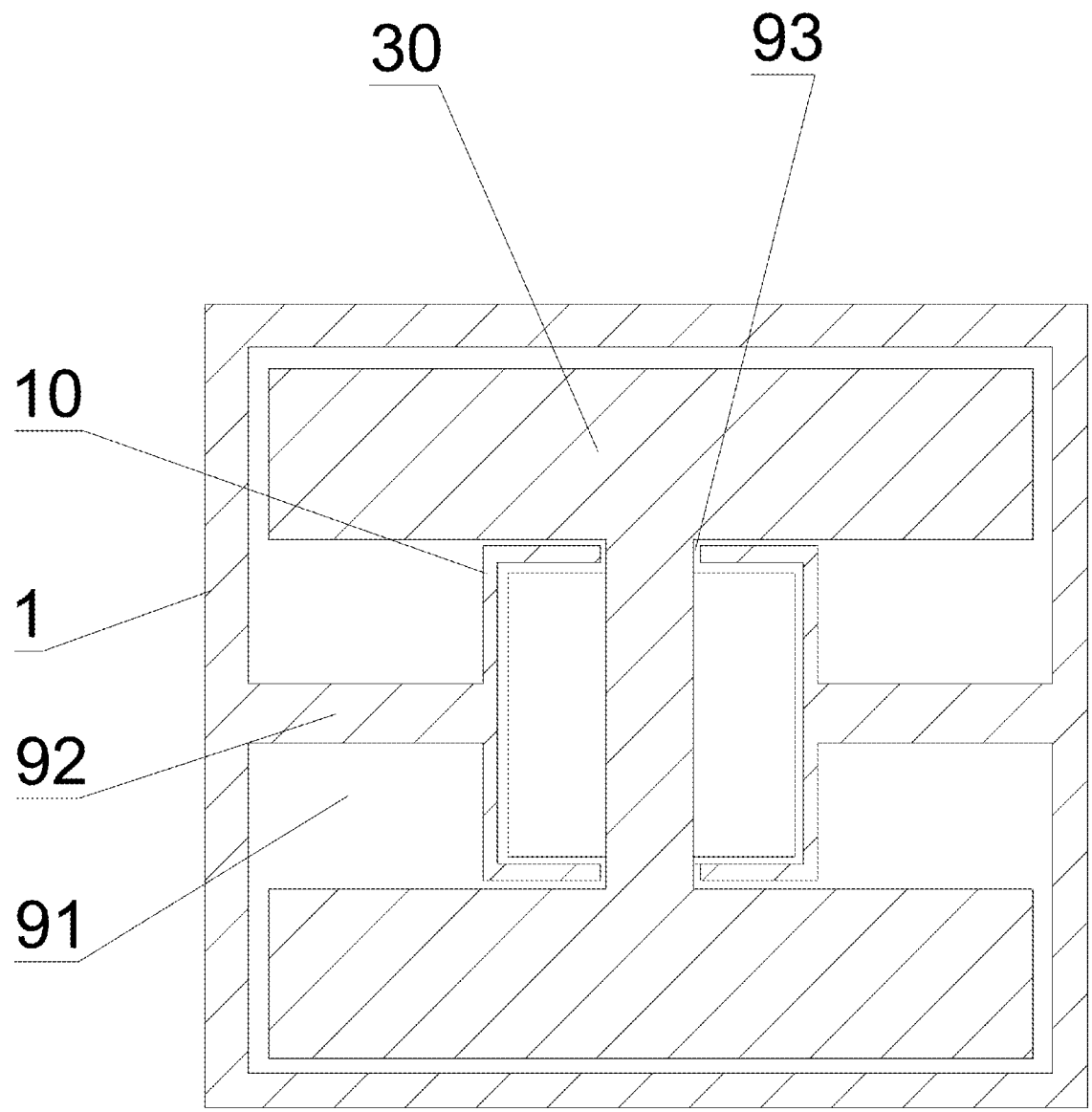
FIG. 5 is a schematic diagram of a transverse section of a pile hammer guide rail, a guide rail for a driven pile and a pile hammer in FIG. 1.
Figure 6:
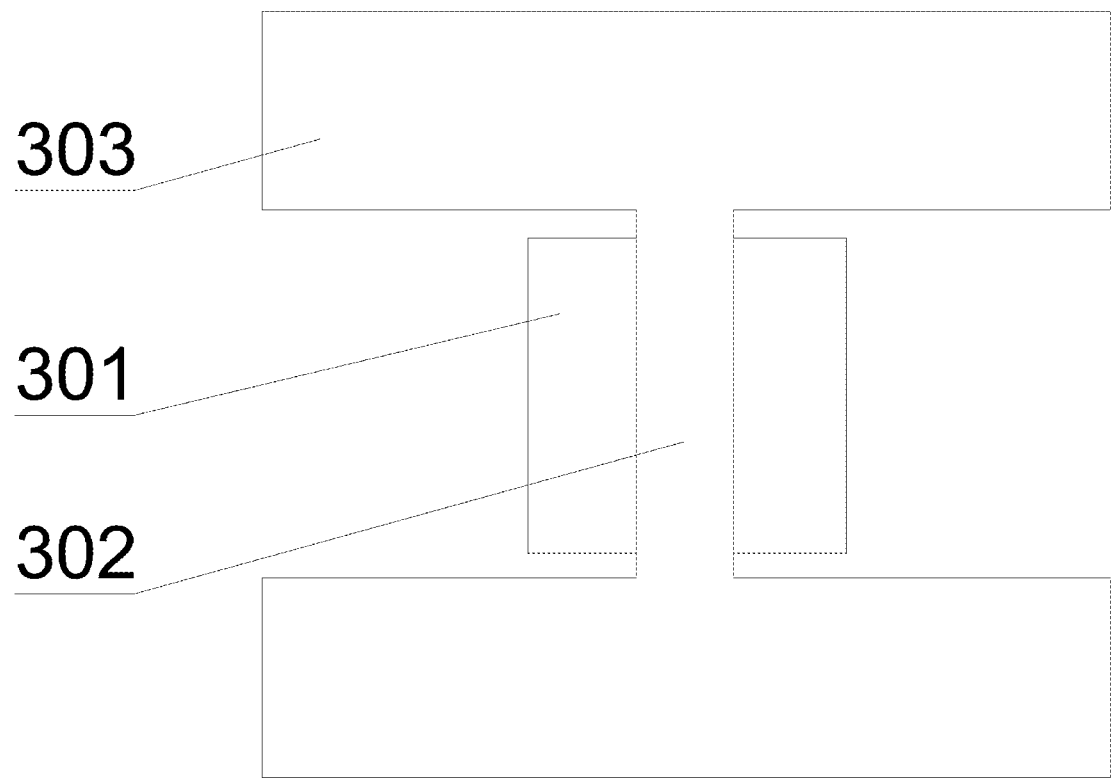
FIG. 6 is a schematic top view of a pile hammer in FIG. 5.
Figure 7:
FIG. 7 is a side view of FIG. 6.
Figure 8:
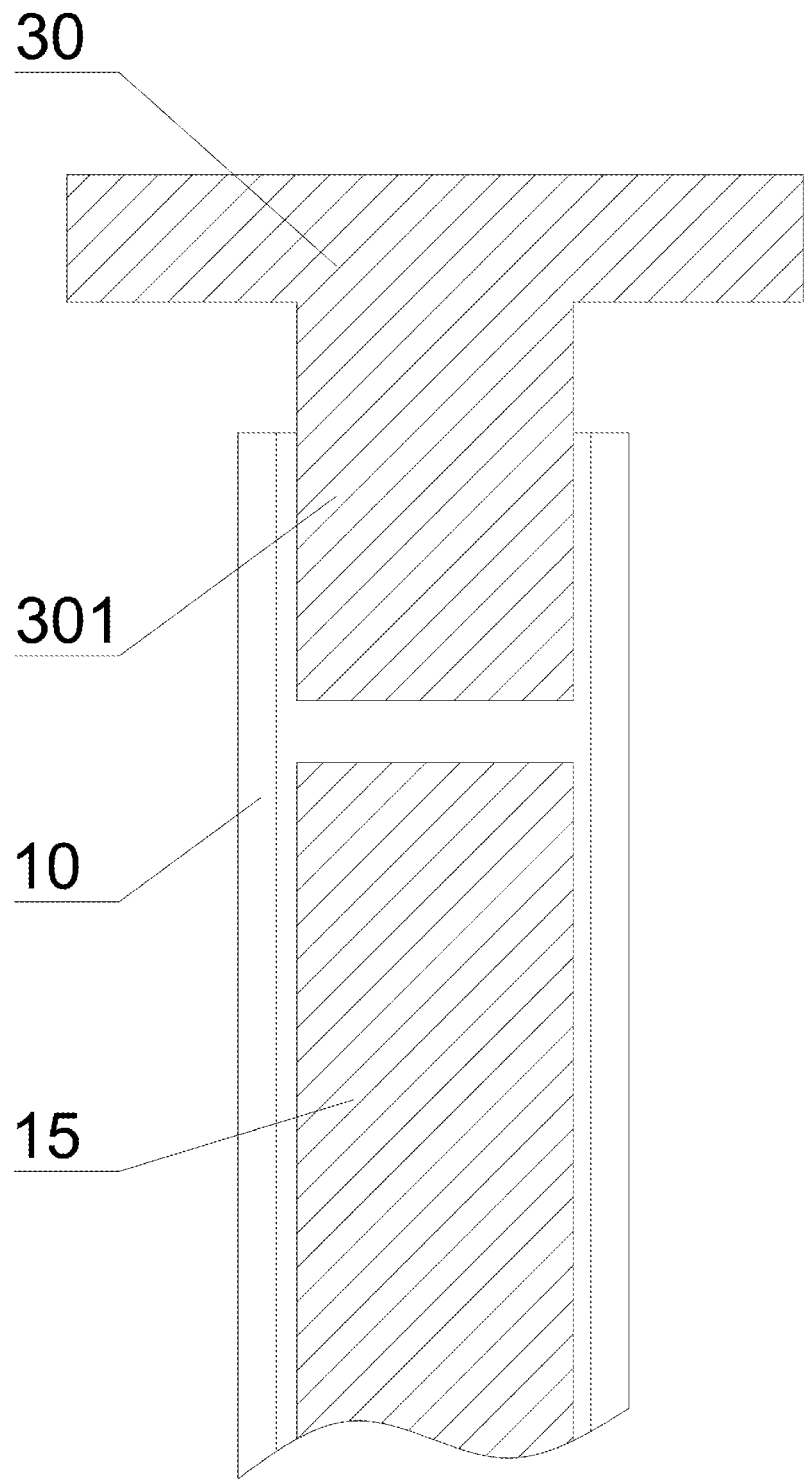
FIG. 8 is a schematic diagram of a structural relationship between a pile hammer, a guide rail for a driven pile and a model pile, where the pile hammer has not entered the guide rail for a driven pile.
Figure 9:
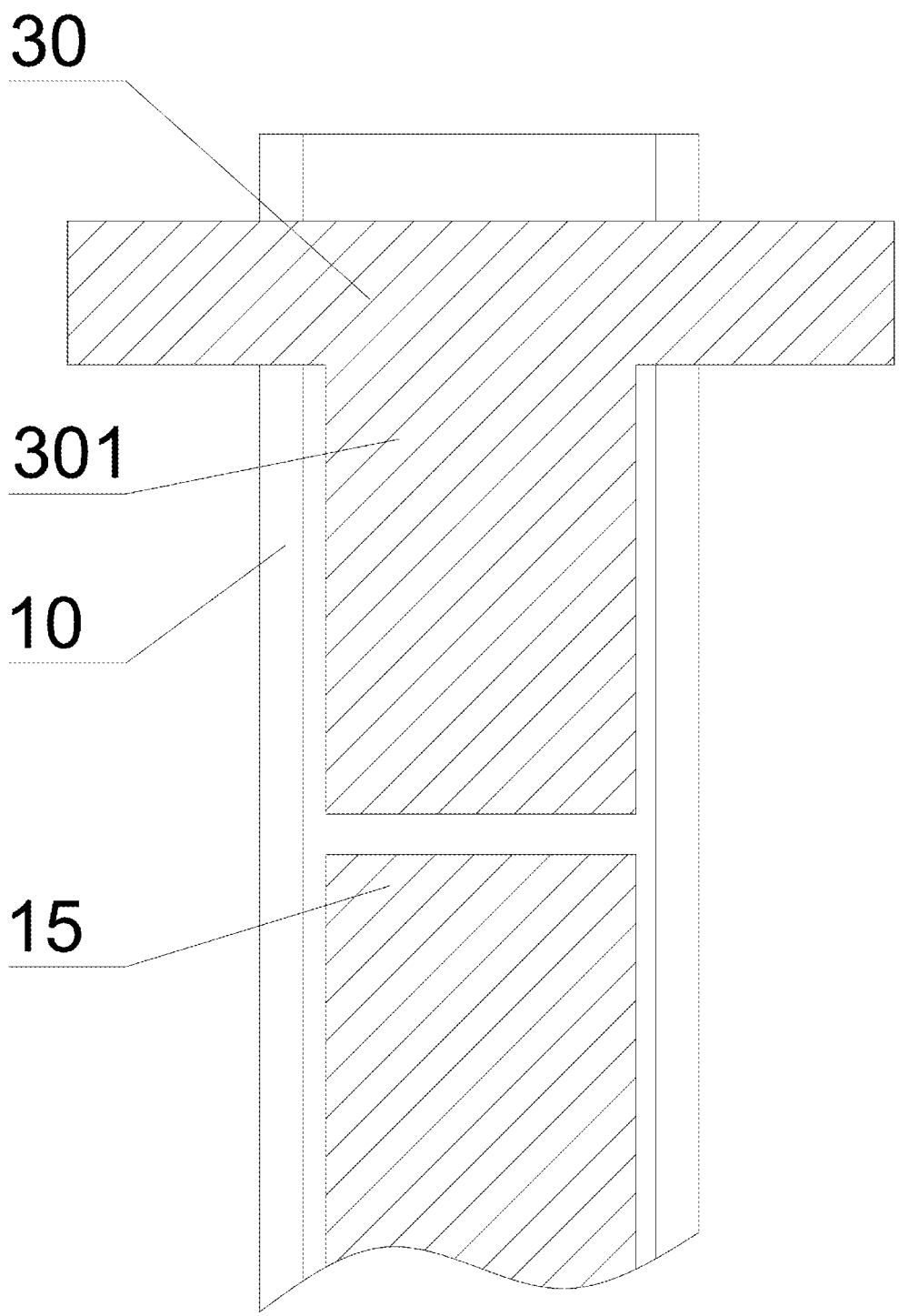
FIG. 9 is a schematic diagram of a structural relationship between a pile hammer, a guide rail for a driven pile and a model pile, where the pile hammer penetrates deeply into the guide rail for a driven pile.

Referring to FIG. 1, FIG. 2, FIG. 5, FIG. 6, FIG. 7 and FIG. 8, to drive the pile hammer and the model pile into the soil more accurately, the pile hammer guide rail 9 includes vertical holes 91 for maintenance at four sides, the pile hammer 30 is placed in the vertical hole, a center of the pile hammer guide rail 9 is provided with the guide rail 10 for a driven pile, two sides of the guide rail 10 for a driven pile are connected to an inner side wall of the pile hammer guide rail 9 through vertical rib plates 92, an upper side and a lower side of the guide rail 10 for a driven pile are provided with side openings 93, a cross section of the pile hammer 30 is I-shaped, the pile hammer 30 has a downward hammering end 301, a section of the hammering end 301 matches the guide rail 10 for a driven pile, the hammering end 301 is placed in the guide rail 10 for a driven pile, an upper narrow part 302 and a lower narrow part 302 of the pile hammer 30 are positioned at the side openings 93, and an upper wide part 303 and a lower wide part 303 of the pile hammer 30 are attached to an inner wall of the pile hammer guide rail 9. In the above-mentioned structure, the I-shaped pile hammer 30 is accurately guided, and the guide rail 10 for a driven pile and the hammering end 301 are arranged at the center of gravity of the pile hammer 30, which not only ensures the volume and weight of the pile hammer 30, but also ensures that the hammering position is below the center of gravity of the pile hammer 30, thus being more efficient and accurate.

Referring to FIG. 1 to FIG. 4, a method for operating the device for centrifuge testing of a driven pile in different installation and pull-out modes provided in the present disclosure includes the following steps.

Step 1: Determine a size and layout of each system of a test device, and perform test analysis of processes of penetration and pull-out of a large-diameter open pile foundation in in-situ saturated clay, where a geotechnical centrifuge is 150 kg, a pile has a diameter of 8 m, a length of 80 m and a wall thickness of 9 cm in in-situ size, the saturated clay is marine saturated clay, and a fluid therein is seawater; a model pile 15 has a diameter of 5.34 cm, a length of 53.34 cm and a wall thickness of 0.6 mm in size, grating fiber points are evenly and symmetrically arranged on a pile body, there are 10 grating fiber points on each side, 3 columns of grating fiber miniature earth pressure cells and 3 columns of osmometers are symmetrically arranged in soil, the two kinds of test elements are arranged at intervals, there are a total of 12 columns of test elements, there are 8 elements in a height direction in each column, a model box has a diameter of 1.5 m and a height of 1.0 m in size, 10 drain holes are evenly formed in a height direction of the model box, 10 drain holes are evenly formed in a diameter direction at the bottom, 15 columns of drain holes are formed in an arc direction, pile driving frames 8 each have a length of 1.2 m and a width of 0.25 m, pile hammer guide rails 9 and guide rails 10 for a driven pile are evenly and symmetrically distributed on the pile driving frames 9, and the pile driving frames 8 are symmetrically fixed in a vertical 8 supporting system in a length direction.

Step 2: Install a supporting system, a pile-soil system, a measurement system and a centrifuge system, where the vertical supporting system and a pile driving frame supporting system are made of 8 #B-12 #B high-strength I-beams anchored by rivets, and the pile driving frame supporting system and the pile driving frame are also anchored by rivets, and the threaded rigid column 1 has a height of 1.8 m and a diameter of 1.2 cm.

Step 3: Install a pile driving system, where the model pile penetrates into the soil through hammering and is pulled out through static pressure, and a corresponding pile hammer and pull-out device are selected and servo-controlled; when hammer penetration is used, a pile pad 13 needs to be laid for the model pile; when static pressure and vibration penetration are used, the pile pad 13 is not required; and when vibration penetration is used, a pile cap 14 and a pile hammer of the model pile need to be fixed.

Step 4: Perform a hammering penetration test, acquire monitored data through a wireless acquisition system, record a hammering penetration process through a high-definition high-speed computer, and control the hammering penetration of the pile hammer through wireless servo control.

Step 5: After the penetration is completed, perform a long-term load-bearing performance test, and enable a pile hammer device to be held tightly with the a pile head through servo control; after a duration which is required by the test and in which data is always acquired, convert the servo control to a pull-out mode, perform a pull-out test, acquire relevant data through a wireless acquisition system, and record the pull-out process with a high-speed camera, where the wireless acquisition system can acquire the data in real time without interfering with the test device, and the high-speed camera can record the pull-out process to better observe and confirm a theoretical model.

The above are only preferred implementations of the present disclosure, and the protection scope of the present disclosure is not limited to the above-mentioned embodiments. All technical solutions under the idea of the present disclosure belong to the protection scope of the present disclosure. It should be pointed out that for a person of ordinary skill in the art, several improvements and polishing made without departing from the principle of the present disclosure should also be regarded as falling within the protection scope of the present disclosure.

What is claimed is:

1. A device for centrifuge testing of a driven pile in different installation and pull-out modes, comprising a supporting system, a pile driving system, a pile-soil system, a centrifuge system and a measurement and acquisition system, wherein the supporting system comprises a vertical supporting system and a pile driving frame supporting system; the vertical supporting system comprises a threaded rigid column, a vertical outer support frame, a vertical inner support frame and a bottom rigid plate; the vertical supporting system is configured to support an entire test model and connected to a corresponding device of the centrifuge, and at the same time provides a supporting platform for a pile driving frame in the model; the vertical outer support frame is movably connected to the threaded rigid column, and is controlled to lift by a vertical support lifting motor; the pile driving frame supporting system is configured to support the pile driving frame and comprises an upper pile driving frame outer support, an upper pile driving frame inner support, a lower pile driving frame inner support, a lower pile driving frame outer support, an upper pile driving frame back support and a lower pile driving frame back support, and the pile driving frame supporting system ensures that the pile driving frame is kept stable in a pile driving process and a geotechnical centrifuge test process;

the pile-soil system comprises a model pile and a model box, a pile cap is fixed at the top of the model pile and protects a pile head of the model pile in a penetration process, an element for monitoring physical and mechanical variables is attached to a pile body, the model box is a semi-cylindrical box body with a closed lower portion and an open upper portion, a semicircular portion is composed of high-strength and high-rigidity steel plates, drain holes are distributed in the box body, a semicircular section of the model box is composed of transparent plates made of a high-strength resin, soil is arranged in the model box, and a lifting motor is arranged below a fixing support and sleeves the threaded rigid column; and the lifting motor drives a nut to rotate to lift on the threaded rigid column, so as to control a height of the fixing support;

the centrifuge system comprises a centrifuge, the supporting system, a full-life loading system of a driven pile and the pile-soil system are fixedly installed in a test cabin of the centrifuge, and the centrifuge system is configured to apply a hypergravity to the test model through movement of the centrifuge upon starting a hammering penetration test, and a time of fluid-solid coupling is shortened in a hypergravity environment to speed up a change process; and the measurement and acquisition system comprises a soil monitoring system and a pile body monitoring system, the soil monitoring system comprises a soil monitoring element, the pile body monitoring system comprises a pile body monitoring element, the soil monitoring element tests an initial stress-strain of a soil sample, a pore pressure state and corresponding physical and mechanical parameters during pile driving and after installation, and the pile body monitoring element is capable of acquiring physical and mechanical parameters;

wherein the pile driving system comprises a pile driving frame, a pile driving device and a penetration and pull-out power device; the pile driving frame is connected to the vertical supporting system through the pile driving frame supporting system, and the pile driving device comprises a pile hammer guide rail and a guide rail for a driven pile; the penetration and pull-out power device is provided with a power system and a pile hammer, and a pile hammer pad is installed on a lower portion of the pile hammer; a pull-out mode is vibration pull-out or static load pull-out, a lower end of a pull-out device is provided with a hammer pad, the hammer pad conducts electricity to generate electromagnetic attraction, and a magnetic force of the hammer pad is controlled by changing a current; the pile cap is made of a magnetically attractable material, the hammer pad is magnetically attracted to the pile cap after being energized, and the pile cap, the hammer pad and the model pile are fixed to be a whole in the pull-out process.

2. The device for centrifuge testing of a driven pile in different installation and pull-out modes according to claim 1, wherein the pile hammer guide rail comprises vertical holes for maintenance at four sides, the pile hammer is placed in the vertical hole, a center of the pile hammer guide rail is provided with the guide rail for a driven pile, two sides of the guide rail for a driven pile are connected to an inner side wall of the pile hammer guide rail through vertical rib plates, an upper side and a lower side of the guide rail for a driven pile are provided with side openings, a cross section of the pile hammer is I-shaped, the pile hammer has a downward hammering end, a section of the hammering end matches the guide rail for a driven pile, the hammering end is placed in the guide rail for a driven pile, an upper narrow part and a lower narrow part of the pile hammer are positioned at the side openings, and an upper wide part and a lower wide part of the pile hammer are attached to an inner wall of the pile hammer guide rail.

3. The device for centrifuge testing of a driven pile in different installation and pull-out modes according to claim 2, wherein the pile driving frame is marked with a ruler.

4. The device for centrifuge testing of a driven pile in different installation and pull-out modes according to claim 1, wherein the pile driving frame is marked with a ruler.

5. A method for operating the device for centrifuge testing of a driven pile in different installation and pull-out modes according to claim 1, comprising the following steps:

step 1: determining a size and layout of each system of a test device, and performing test analysis of processes of penetration and pull-out of a large-diameter open pile foundation in in-situ saturated clay, wherein the centrifuge has an acceleration which is 150 times an earth gravitational acceleration g, a pile has a diameter of 8 m, a length of 80 m and a wall thickness of 9 cm in in-situ size, the saturated clay is marine saturated clay, and a fluid therein is seawater; a model pile has a diameter of 5.34 cm, a length of 53.34 cm and a wall thickness of 0.6 mm in size, grating fiber points are evenly and symmetrically arranged on a pile body, there are 10 grating fiber points on each side, 3 columns of grating fiber miniature earth pressure cells and 3 columns of osmometers are symmetrically arranged in soil, the two kinds of test elements are arranged at intervals, there are a total of 12 columns of test elements, there are 8 elements in a height direction in each column, a model box has a diameter of 1.5 m and a height of 1.0 m in size, 10 drain holes are evenly formed in a height direction of the model box, 10 drain holes are evenly formed in a diameter direction at the bottom, 15 columns of drain holes are formed in an arc direction, pile driving frames each have a length of 1.2 m and a width of 0.25 m, pile hammer guide rails and guide rails for a driven pile are evenly and symmetrically distributed on the pile driving frames, and the pile driving frames are symmetrically fixed in a vertical supporting system in a length direction;

step 2: installing a supporting system, a pile-soil system, a measurement and acquisition system and a centrifuge system;

step 3: installing a pile driving system, wherein the model pile penetrates into the soil through hammering and is pulled out through static pressure, and a corresponding pile hammer and pull-out device are selected and servo-controlled;

step 4: performing a hammering penetration test, acquiring monitored data through a wireless acquisition system, recording a hammering penetration process through a high-definition high-speed computer, and controlling the hammering penetration of the pile hammer through wireless servo control; and step 5: after the penetration is completed, performing a long-term load-bearing performance test, and enabling a pile hammer device to be held tightly with the a pile head through servo control; after a duration which is required by the test and in which data is always acquired, converting the servo control to a pull-out mode, performing a pull-out test, acquiring relevant data through a wireless acquisition system, and recording the pull-out process with a high-speed camera.

6. The method for operating the device for centrifuge testing of a driven pile in different installation and pull-out modes according to claim 5, wherein when hammer penetration is used, a pile pad needs to be laid for the model pile; when static pressure and vibration penetration are used, the pile pad is not required; and when vibration penetration is used, a pile cap and a pile hammer of the model pile need to be fixed.

7. The method for operating the device for centrifuge testing of a driven pile in different installation and pull-out modes according to claim 6, wherein the vertical supporting system and a pile driving frame supporting system are made of 8 #B-12 #B high-strength I-beams anchored by rivets, and the pile driving frame supporting system and the pile driving frame are also anchored by rivets.

8. The method for operating the device for centrifuge testing of a driven pile in different installation and pull-out modes according to claim 5, wherein the vertical supporting system and a pile driving frame supporting system are made of 8 #B-12 #B high-strength I-beams anchored by rivets, and the pile driving frame supporting system and the pile driving frame are also anchored by rivets.

* * * * *